United States Patent [19]

Karol

[11] Patent Number: 4,761,482

[45] Date of Patent: Aug. 2, 1988

[54] TERPENE DERIVATIVES OF 2,5-DIMERCAPTO-1,3,4-THIADIAZOLES AND LUBRICATING COMPOSITIONS CONTAINING SAME

[75] Inventor: Thomas J. Karol, Norwalk, Conn.

[73] Assignee: R. T. Vanderbilt Company, Inc., Norwalk, Conn.

[21] Appl. No.: 41,496

[22] Filed: Apr. 23, 1987

[51] Int. Cl.$^4$ .......................................... C07D 285/12
[52] U.S. Cl. .................................. 548/142; 252/46.4; 252/47; 252/47.5
[58] Field of Search ................. 548/142; 252/46.4, 47, 252/47.5

[56] References Cited

U.S. PATENT DOCUMENTS

| | | | |
|---|---|---|---|
| 2,736,729 | 2/1956 | Krzikalla et al. | 260/302 |
| 2,764,547 | 9/1956 | Fields | 252/32.7 |
| 3,212,892 | 10/1965 | König | 548/142 |
| 3,609,079 | 9/1971 | Devine et al. | 252/46.3 |
| 4,410,436 | 10/1983 | Holstedt et al. | 252/46.4 |

FOREIGN PATENT DOCUMENTS 943790  6/1956  Fed. Rep. of Germany.

OTHER PUBLICATIONS

Fields, *Addition of 1,3,4-Thiadiazole-2,5-dithiol to Olefinic Compounds,* 21J. Org. Chem. 497–9 (1956).

*Primary Examiner*—Robert Gerstl
*Attorney, Agent, or Firm*—Rasma B. Balodis

[57] ABSTRACT

Disclosed are reaction products of terpene compounds and 2,5-dimercapto-1,3,4-thiadiazole. The reaction products are useful as antiwear agents and antioxidants in lubricating compositions.

5 Claims, No Drawings

TERPENE DERIVATIVES OF 2,5-DIMERCAPTO-1,3,4-THIADIAZOLES AND LUBRICATING COMPOSITIONS CONTAINING SAME

BACKGROUND OF THE INVENTION

The present invention concerns novel derivatives of thiadiazole compounds. More particularly, the new thiadiazoles are derived from 2,5-dimercapto-1,3,4-thiadiazole and terpene compounds. The invention further concerns improved lubricating compositions containing certain reaction products of 2,5-dimercapto-1,3,4-thiadiazole and terpene compounds.

Additives known as antiwear agents are employed to increase the load-carrying capacity of lubricants. The antiwear agents promote the formation of a surface film and thereby prevent wear of the contacting surfaces.

During the course of use, lubricants are susceptible to deterioration due to oxidation. The oxidative process leads to the loss of lubricating properties and inadequate protection of the device to be lubricated. Antioxidants are added to inhibit the oxidative process. Thus, it is desirable that antiwear agents possess antioxidant properties.

The most commonly used additives to exhibit antiwear and antioxidant properties are zinc dihydrocarbylphosphorodithioates. However, due to stricter environmental controls, it is particularly desirable to reduce the phosphorus content in lubricants. There is a need to develop improved lubricating compositions that are environmentally sound.

It has been surprisingly discovered that the foregoing disadvantages of the prior art lubricants can be eliminated by replacing all or part of the phosphorus-containing additive with certain terpene derivatives of 2,5-dimercapto-1,3,4-thiadiazoles. Particularly useful are novel 2-terpene derivatives of 5-hydrocarbylthio-2-mercapto-1,3,4-thiadiazoles and the known mono- and diterpene derivatives of 2,5-dimercapto-1,3,4-thiadiazoles. The latter have been disclosed as corrosion inhibitors in U.S. Pat. No. 2,764,547 to Fields.

SUMMARY OF THE INVENTION

In accordance with the invention, there are provided novel reaction products of terpene and 2,5-dimercapto-1,3,4-thiadiazole having the structural formula

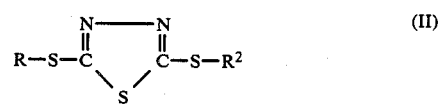
(I)

wherein R represents pinene residue having the structural formula

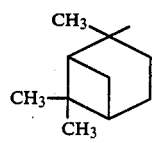

and limonene residue having the structural formula

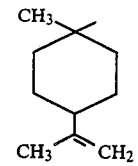

and R' represents alkyl, hydroxyalkyl, alkylthio, phenylalkyl and alkylated phenylalkyl groups.

Another aspect of the invention concerns oil-based and water-based lubricating compositions comprising a major amount of base oil or water and (a) an amount sufficient to impart antiwear and antioxidant properties of compounds having the structural formula $$\underset{\underset{S}{\diagdown\diagup}}{R-S-\overset{N-\!\!\!-\!\!\!-N}{\overset{\|}{C}}\overset{\|}{C}-S-R^2}\qquad(II)$$

wherein R represents pinene and limonene residues as defined hereinabove and $R^2$ may be the same as R or hydrogen, alkyl, hydroxyalkyl, alkylthio, phenylalkyl and alkylated phenylalkyl groups and (b) 0 to about 1.0 percent by weight of zinc dihydrocarbylphosphorodithioate.

DESCRIPTION OF SPECIFIC EMBODIMENTS

The reaction products of the invention may be prepared by reacting one mole of 2,5-dimercapto-1,3,4-thiadiazole with one to two moles of terpene according to the method described in U.S. Pat. No. 2,764,547. The novel products may be prepared by reacting one mole of 2,5-dimercapto-1,3,4-thiadiazole with terpene at about 80° C. to 170° C. followed by alkylation by known methods. Alternately, the two reactions may be performed in a reversed order. The 2-hydroxyalkyl substituted derivatives may be prepared by reacting 2,5-dimercapto-1,3,4-thiadiazole with the corresponding epoxide. The reaction may be conducted in the presence of an inert solvent such as alcohols, toluene and benzene and reaction promoter as for example, alkyl sulfonic acids. The reaction temperature will depend upon the specific reactants and solvent media employed. Typically reaction temperature will range from about 180° C. to 140° C.

The alkyl groups R' and $R^2$ in the formulae I and II represent an alkyl group having from 1 to 50 carbon atoms and a straight and branched chain including alkyls substituted by a hydroxy group and an aryl group. These include, among others, methyl, ethyl, n-propyl, isopropyl, n-butyl, isobutyl, sec-butyl, pentyl, octyl, dodecyl, octadecyl, benzyl, betaphenylethyl, and 2-hydroxyhexadecyl groups.

The terpene derivatives of the invention are useful as lubricating additives. The compounds possess multifunctional properties with respect to antiwear and oxidation inhibition. For some applications such as motor crankcase oil, the compounds provide particularly suitable lubricity improvement in lubricating compositions when used in combination with zinc dihydrocarbylphosphorodithioate.

The zinc dihydrocarbylphosphorodithioates may be represented by the following formula

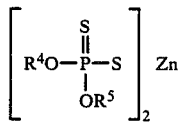

wherein $R^4$ and $R^5$ may be the same or different hydrocarbyl group containing from 1 to 18 carbon atoms and including such groups as alkyl, alkenyl, aryl, aralkyl, alkaryl and cycloaliphatic groups. The zinc dihydrocarbylphosphorodithioates are known compounds. They may be prepared according to known methods by esterifying phosphorodithioic acid, usually by reaction of an alcohol or phenol with $P_2S_5$ and then neutralizing with a zinc compound such as zinc oxide.

The lubricating compositions contemplated herein include lubricating oils and lubricating greases containing a major amount of base oil. The base oil may be selected from oils derived from petroleum hydrocarbon and synthetic sources. The hydrocarbon base oil may be selected from napthenic, aromatic, and paraffinic mineral oils. The synthetic oils may be selected from, among others, alkylene polymers, polysiloxanes, carboxylic acid esters and polyglycol ethers.

Another lubricating composition useful herein includes water based systems. Typically the aqueous systems comprise at least 40 percent of water and zero to less than 15 percent of base oil. Oil-soluble additives are incorporated in the system with the aid of solubilizer/stabilizer systems. The water based systems are useful not only as lubricants, but also as functional fluids such as cutting oils, hydraulic fluids, and transmission fluids.

The amount of the terpene additive required to be effective for imparting antiwear and antioxidant characteristics in lubricating compositions may range from about 0.01 to 10 percent of the lubricating composition. The preferred range is 0.1 to 5 percent of the additive of the total lubricating composition.

In general, zinc dihydrocarbylphosphorodithioates have been added to lubricating compositions up to 5% of the lubricating composition. When used with the present terpene additives, the amount may be reduced to as low as 0.1 and preferably 0.5 parts by weight per hundred parts of the lubricating base.

The lubricating compositions may contain the necessary ingredients to prepare the composition as for example dispersing agents, emulsifiers, and viscosity improvers. Greases may be prepared by addition of thickeners as for example salts and complexes of fatty acids, polyurea compounds, clays and quarternary ammonium bentonite. Depending on the intended use of the lubricant, other funtional additives may be added to enhance a particular property of the lubricant. The lubricating compositions may further contain known antioxidants, extreme pressure agents, metal passivators, rust inhibitors and other antiwear agents.

The following examples are given for the purpose of further illustrating the invention. All percentages and parts are based on weight unless otherwise indicated.

EXAMPLE 1

2-(2-Pinanylthio)-5-(octyldithio)-1,3,4-thiadiazole

Alpha-pinene (38 g, 0.28 mol) and 2,5-dimercapto-1,3,4-thiadiazole (40 g, 0.27 mol) were charged to the reaction flask and cautiously heated to 155° C. since the reaction was exothermic. The reaction was maintained at 155° C. for 15 min. and then cooled. Isopropanol (32 g) and n-octylmercaptan (43.7 g, 0.30 mol) were charged. Hydrogen peroxide, 35% (60 g, 0.62 mol) was added slowly while maintaining the temperature at 40°-50° C. The reaction was then allowed to stand overnight. The product was extracted with 150 ml of n-hexane and washed with 150 ml of 1M sodium carbonate. The organic layer was dried over magnesium sulfate, filtered, and the solvent removed by rotary evaporation.

EXAMPLE 2

2-(2-Pinanylthio)-5-(2-hydroxyhexadecylthio)-1,3,4-thiadiazole 2,5-Dimercapto-1,3,4-thiadiazole (161.3 g, 1.08 mol) and alphapinene (161.3 g, 1.18 mol) were charged to a reaction vessel and cautiously heated to 120° C. (exothermic reaction). The reaction was maintained at 135° C. for one hour. The intermediate product was stripped under vacuum at 135° C. to remove any unreacted pinene and filtered hot. Methanol (200 ml), hexane (150 ml) and water (15 ml) were charged. The hexane layer was removed and discharded. The methanol layer was stripped of methanol by rotary evaporation and the intermediate product residue was mixed with toluene (200 ml) and then extracted with 1M sodium bicarbonate solution (50 ml). The toluene layer was dried over magnesium sulfate and the solvent removed by rotary evaporation. The yield was 134.1 g (0.468 mol) of the purified intermediate, 2-(2-pinanylthio)-5-mercapto-1,3,4-thiadiazole. This product was reacted with 1,2-epoxyhexadecane (112.3 g, 0.468 mol) by charging both reagents and isopropanol (100 ml) and bringing the reaction to reflux. The solvent was then stripped by rotary evaporation to afford the product.

EXAMPLE 3

2-(2-Pinanylthio)-5-(2-hydroxyethylthio)-1,3,4-thiadizole 2,5-Dimercapto-1,3,4-thiadiazole (61.47 g, 0.47 mol), alpha-pinene (62.12 g, 0.45 mol), and acidified calcium sulfonate catalyst (TLA-256, manufactured by Texaco Chemical Co., 3 g) were charged to the reaction vessel. The reaction was cautiously heated to 155° C. (exothermic reaction) and maintained at this temperature for 0.5 hours. After cooling, isopropanol (150 ml) was added and the reaction was refluxed. Ethylene oxide (20 g, 0.45 mol) was bubbled in while the reaction refluxed. The product was isolated by stripping off the solvent through rotary evaporation.

EXAMPLE 4

2-(2-Pinanylthio)-5-(1-methyl-1-phenyl)ethylthio-1,3,4-thiadiazole 2,5-Dimercapto-1,3,4-thiadiazole (30.0 g, 0.2 mol) and alphamethylstyrene (23.7 g, 0.2. mol) were charged to a reaction vessel and cautiously heated to 120° C. (exothermic reaction). The reaction was then maintained at 120°-140° C. for 15 min. Alpha-pinene (30 g, 0.22 mol) was charged and the reaction was heated to 155° C. and maintained 2 hours at this temperature. The product was then filtered using a filter aid.

EXAMPLE 5

2-(2-Pinanylthio)-5-(t-butylthio)-1,3,4-thiadiazole 2,5-Dimercapto-1,3,4-thiadiazole (35 g, 0.23 mol) and alpha-pinene (35 g, 0.26 mol) were charged to a reaction vessel and heated cautiously to 140° C. (exothermic reaction). The reaction was maintained at 135°-155° C. for 15 min. The reaction was fitted with a Dean Stark trap filled with xylene. Xylene (15 ml) was charged to the reaction. The reaction was fitted with an addition funnel containing t-butanol (25 g, 0.34 mol). The alcohol was added slowly with the reaction refluxing. Sulfuric acid (3 drops) was added to accelerate the water removal. The reaction product was isolated after approximately 5 ml (about 0.25 mol) of water were collected. Solvent was stripped by rotary evaporation. The product was mixed with calcium hydroxide (1 g), hexane (about 100 ml), and sufficient acetone (about 50 ml) to maintain one liquid layer. The product was filtered using a filter aid and the solvent removed by rotary evaporation. This afforded the final product.

EXAMPLE 6

The additives of the invention were evaluated by the following tests

1. Shell Four-Ball Wear Test

The test was conducted essentially according to the method described in ASTM D-2266 procedure. Four highly polished steel balls 12.5 mm in diameter were placed in a test cup and submerged in the test sample. The test oil was Sunvis TM 21 manufactured by Sun Oil Company. The test was carried out at a rotation speed of 1800 rpm under a load of 40 kg at 54.5° C. Although not a quantitative tool for measuring wear, the test was designed to determine qualitatively the lowest amount of additive that afforded wear protection. A rating of "failed" was assigned to scars measuring greater than 1.0 mm in diameter and "passed" to those measuring less than 1.0 mm in diameter.

TABLE I

FOUR-BALL WEAR TEST

| Sample | Active Ingredient | Percent | Scar Protection |
|---|---|---|---|
| 1 | None | — | failed |
| 2 | Zinc di(2-ethylhexyl) phosphorodithioate | 0.05 | failed |
| 3 | Zinc di(2-ethylhexyl) phosphorodithioate | 0.10 | passed |
| 4 | 2-(2-Pinanylthio)-5-(octyldithio)-1,3,4-thiadiazole | 0.05 | passed |
| 5 | 2-(2-Pinanylthio)-5-(2-hydroxyhexadecylthio)-1,3,4-thiadiazole | 0.05 | passed |
| 6 | 2-(2-Pinanylthio)-5-(1-methyl-1-phenyl)ethylthio-1,3,4-thiadiazole | 0.05 | passed |
| 7 | 2,5-Bis(2-pinanylthio-1,3,4-thiadiazole | 0.05 | passed |
| 8 | 2-(2-Limonanylthio)-5-(2-hydroxyhexadecylthio)-1,3,4-thiadiazole | 0.05 | passed |

2. Thin Film Oxygen Uptake Test

The test was conducted essentially according to the method described by Chia-soon Ku et al., *J. Am. Soc. Lubricating Eng.*, 40, 2, 75-83, 1984. The oxidation induction time of the lubricant was measured under conditions which simulate the high temperature oxidation processes in automative engines by a modified rotary bomb oxidation test method ASTM D-2272. The test was conducted with 1.5 gram samples of SAE 30 SF/CC motor oil with catalyst obtained from the National Bureau of Standards. The oil contained 0.11% phosphorus. Additives of the invention were added to the oil in the amount indicated in Table II. The test was conducted at 160° C. and initial oxygen pressure of 620.6 kPa (90 psi). A "pass" oil has a high induction time, while a "fail" oil has a low induction time. The additives of the invention have good antioxidant properties as shown by data compiled in Table II.

TABLE II

THIN FILM OXYGEN UPTAKE TEST

| Sample | Active Ingredient | Percent | Average Induction Time, min. |
|---|---|---|---|
| 9 | None | — | 55.0 |
| 10 | 2-(2-Pinanylthio)-5-(2-hydroxyhexadecylthio)-1,3,4-thiadiazole | 0.35 | 87.5 |
| 11 | 2,5-Bis(2-pinanylthio)-1,3,4-thiadiazole | 0.35 | 122.0 |
| 12 | 2-(2-Limonanylthio)-5-(2-hydroxyhexadecylthio)-1,3,4-thiadiazole | 0.35 | 103.0 |

The above embodiments have shown various aspects of the present invention. Other variations will be evident to those skilled in the art and such modifications are intended to be within the scope of the invention as defined by the appended claims.

What is claimed is:

1. A compound having the structural formula

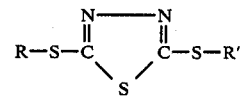

wherein R represents pinene residue having the structural formula

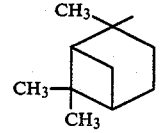

and limonene residue having the structural formula

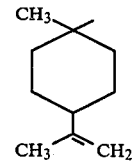

and R' represents alkyl, hydroxyalkyl, alkylthio, phenylalkyl and alkylated phenylalkyl groups wherein the alkyl group contains 1 to 50 carbon atoms.

2. A composition comprising a major proportion of oil of lubricating viscosity wherein said oil is a petroleum hydrocarbon oil or a synthetic oil and from about 0.01 to 10 percent by weight of a compound having the structural formula

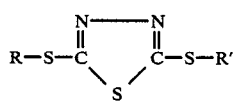

wherein R represents pinene residue having the structural formula

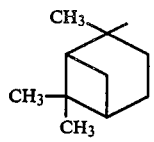

and limonene residue having the structural formula

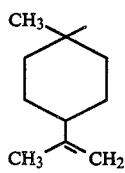

and R' represents alkyl, hydroxyalkyl, alkylthio, phenylalkyl and alkylated phenyl groups wherein the alkyl group contains 1 to 50 carbon atoms.

3. A composition according to claim 2 which further contains up to 1.0 percent by weight of zinc dihydrocarbylphosphorodithioate wherein the hydrocarbyl groups are selected from the group consisting of alkyl, alkenyl, aryl, aralkyl, alkaryl and cycloaliphatic groups.

4. A composition comprising at least 40 percent by weight of water, from 0 to 15 percent by weight of petroleum hydrocarbon oil or a synthetic oil and from about 0.01 to 10 percent by weight of a compound having the structural formula

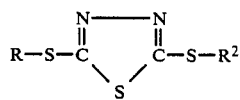

wherein R represents pinene residue having the structural formula

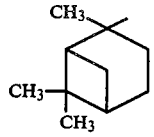

and limonene residue having the structural formula

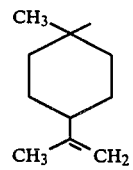

and $R^2$ may be same as R or hydrogen, alkyl, hydroxyalkylthio, phenylalkyl and alkylated phenylalkyl groups wherein the alkyl group contains 1 to 50 carbon atoms.

5. A composition according to claim 4 which further contains up to 1.0 percent by weight of zinc dihydrocarbylphosphorodithioate wherein the hydrocarbyl groups are selected from the group consisting of alkyl, alkenyl, aryl, aralkyl, alkaryl and cycloaliphatic groups.

* * * * *

UNITED STATES PATENT AND TRADEMARK OFFICE
CERTIFICATE OF CORRECTION

PATENT NO. :   4,761,482
DATED      :   Aug. 2, 1988
INVENTOR(S) :  Thomas J. Karol It is certified that error appears in the above-identified patent and that said Letters Patent are hereby corrected as shown below:

Column 2, line 49
"180° C. to 140° C." should be --80° C. to 140° C.--;

Column 2, line 57
"betaphenylethyl" should be --beta-phenylethyl--;

Column 4, line 17
"alphapinene" should be --alpha-pinene--;

Column 4, line 62
"alphamethylstyrene" should be --alpha-methylstyrene--.

Signed and Sealed this

Seventh Day of February, 1989

Attest:

DONALD J. QUIGG

Attesting Officer      Commissioner of Patents and Trademarks